United States Patent [19]
Albrecht et al.

[11] 4,107,318
[45] Aug. 15, 1978

[54] FUNGICIDAL DISPERSIONS OF A SYSTEMIC FUNGICIDE

[75] Inventors: Konrad Albrecht, Fischbach, Taunus; Heinz Frensch, Frankfurt am Main; Kurt Härtel, Hofheim, Taunus, all of Germany

[73] Assignee: Hoechst Aktiengesellschaft, Frankfurt am Main, Germany

[21] Appl. No.: 786,495

[22] Filed: Apr. 11, 1977

Related U.S. Application Data

[63] Continuation of Ser. No. 634,657, Nov. 24, 1975, abandoned, which is a continuation of Ser. No. 519,039, Oct. 29, 1974, abandoned.

[30] Foreign Application Priority Data

Oct. 31, 1973 [DE] Fed. Rep. of Germany ....... 2354467

[51] Int. Cl.$^2$ ............................................. A01N 9/22
[52] U.S. Cl. ................................ 424/273 R; 424/168; 424/DIG. 8
[58] Field of Search .................. 424/273, 168, DIG. 8

[56] References Cited

U.S. PATENT DOCUMENTS

| 3,657,443 | 4/1972 | Klopping | 424/273 |
| 3,930,010 | 12/1975 | Klopping | 424/273 |

*Primary Examiner*—V. D. Turner
*Attorney, Agent, or Firm*—Curtis, Morris & Safford

[57] ABSTRACT

Oily dispersions having an improved systemic fungicidal activity are composed of about 5 to 30% by weight of BCM, about 60 to 85% by weight of an aliphatic mineral oil having a flash point of from 65° to 180° C and a viscosity of from 1.5 to 30 centipoise at 20° C, about 6 to 15% by weight of a combination of dispersible agents comprising a monoalkylphenol polyglycol ether having from 8 to 12 carbon atoms and a triisobutylphenol polyglycol ether and about 0.1 to 3% by weight of calcium ($C_8 - C_{15}$) monoalkylbenzene sulfonate.

3 Claims, No Drawings

FUNGICIDAL DISPERSIONS OF A SYSTEMIC FUNGICIDE

This is a continuation of application Ser. No. 634,657, filed Nov. 24, 1975, which, in turn, is a continuation of application Ser. No. 519,039, filed Oct. 29, 1974, both of which are abandoned.

The present invention relates to fungicidal dispersions of 2-benzimidazole methylcarbamate (BCM) of the formula

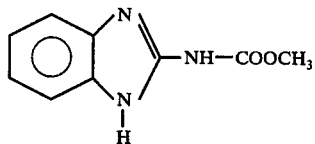

It is known from British Patent Specification No. 1,190,614 that BCM has excellent properties as a systemic plant fungicide. Because of its complete insolubility in lipoids, however, it does not penetrate easily through the plant surface into the interior of the plant where it can display its systemic activity. As a consequence, much of the material remains on the outer plant surface where it acts as a prophylactic fungicide only and is subject to the deteriorating influence of the weather.

The British patent describes a number of ways by which the penetrating capacity of BCM and hence its systemic activity may be improved, such as grinding it to a very fine particle size (below 5 microns) or adding larger-than-usual amounts of so-called "penetrants", i.e. compounds that facilitate the penetration of BCM into the plant interior. However, while these measures remove the drawbacks described above, they create others. For instance, dry milling to a very fine particle size requires special types of mills and expensive filtering apparatus, and the addition of large amounts of penetrants may cause toxicity hazards in the treated plants. Especially, it has not been possible to produce useful dispersions of BCM by the ways described in the British patent.

Such dispersions have a number of advantage over usual formulations such as dusts and wettable powders.

Since for making dispersions the active compounds are ground in the wet state as slurries they do not require expensive filtering devices. Furthermore, dispersions are more easily dosable and do not dust while handling, thus reducing the hazards of toxicity to humans.

The preparation of stable dispersions is difficult. In order to prevent premature sedimentation, the active compounds have to be ground very finely. In this state, however, strong Van der Waal's attraction forces appear between the dispersed particles causing aggregation and flocculation of the particles. To prevent this a surface active agent is usually added which concentrates at the solid-liquid interface and forms a solvating envelope around the individual particles carrying uniform electric charges and thus preventing agglomeration. Even so, however, the solvating envelope may break down partially e.g. if the dispersion is kept at higher temperatures over prolonged periods of time, which results in increasing viscosity, flocculation and irreversible sedimentation.

It is an object of the present invention to provide stable oily dispersions of BCM.

It is a further object of the invention to provide oily dispersions of BCM which have an improved systemic fungicidal activity as compared with previously described BCM-formulations and which are equal to the most active standard plant fungicides such as Benomyl (1-n-butylcarbamoyl-2-methoxy-carbonyl-amino-benzimidazol).

The fungicidal oily dispersions of the invention are characterized by a content of a. about 5 to 30% by weight of a compound of the formula

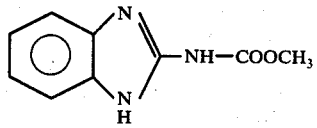

b. about 60 to 85% by weight of an aliphatic mineral oil having a flash point of from 65° to 180° C and a viscosity of from 1.5 to 30 centipoise at 20°, c. about 6 to 15% by weight of a combination of dispersible agents comprising a monoalkylphenol polyglycol ether having from 8 to 12 carbon atoms and a triisobutylphenol polyglycol ether and d. about 0.1 to 3% by weight of calcium ($C_8$–$C_{15}$) monoalkylbenzene sulfonate.

Suitable mineral oils are, for example, aliphatic and/or alicyclic hydrocarbons or mixtures thereof, especially technical grade mineral oils consisting essentially of straight-chain aliphatic or of alicyclic hydrocarbons. Such mineral oils are, for instance Essobayol®, e.g. Essobayol 50, Essobayol 80 and Essobayol 90, Shellsol K®, BP-n-Paraffine I and BP-n-Paraffine III. These mineral oils have viscosities between 1.5 and 29.5 centipoise, flash points between 66° and 178° C, boiling ranges between 192° and about 420° C and paraffine contents above 95% until 100%.

Suitable monoalkylphenol polyglycol ethers are especially those having 8 to 9 carbon atoms in the alkyl moiety and variable degrees of ethoxylation, preferably 8 to 12 ethylene oxide (AeO) units. Examples of such compounds are the types commercially available under the trade name "Triton®", for example Triton X-45, X-114 and X-207. Their proportion in the total formulation is advantageously from 5 to 10% by weight. The triisobutylphenol polyglycol ethers which are also required are commercially available under the trade name "Sapogenat®", for example Sapogenat T 100, T 110 or T 150, where the polyglycol portion has a degree of polymerization of from 8 to 15, preferably of from 10 to 11. These compounds are preferably used in amounts of 1 to 5% by weight.

Calcium salts of the higher monoalkylbenzene sulfonates are used as additives to the dispersions owing to their oil-solubility. Especially preferred are calcium salts of ($C_{10}$–$C_{12}$) monoalkylbenzene sulfonic acids, particularly of dodecylbenzene sulfonic acid.

The Ca-alkylbenzene sulfonates may be added as solids or, preferably, in alcoholic solution, for example in isopropanol or isobutanol.

The oily dispersions of the invention are prepared in known manner, for example by grinding the starting material in ball mills by means of quartz pearls having a diameter of from 1 to 2 mm. The active ingredient in the dispersions obtained has a particle size of less than 10, preferably of less than 5 microns.

The compsition of the emulsifier is critical for the properties of the formulation. Comparative tests have shown that commonly used emulsifiers such as polyglycol esters of oleic acid, stearic acid or palmitic acid, polyglycol derivatives of dodecylmercaptan, of oleylamines or stearylamines do not form storable dispersions with BCM. The same applies to polyglycol ethers of oleyl, stearyl and technical coconut fat alcohols and of dodecylalcohol, of varying degrees of polymerization. Tests with emulsifiers of the type of polyoxethylene sorbitan having varying degrees of polymerization gave also unsatisfactury results. Alkylphenol polyglycol ethers used alone were likewise unsuitable.

The dispersions according to the invention on the other hand are distinguished by an excellent activity and a high storability. In this respect they are considerably superior to the dispersions known from British Patent Specification No. 1,190,614 (example 5). Their efficiency is also superior to known wettable powder formulations of BCM and to Benomyl formulations, as the following examples illustrate.

EXAMPLE 1 (Comparative agent 1)

According to example 5 of British Patent Specification No. 1,190,614 a dispersion was prepared containing 26% by weight of BCM
38.57% by weight of indene resin (Piccolyte resin S-10)
26.43% by weight of low boiling isoparaffin oil (Soltrol 130 ®)
9% by weight of lauryl alcohol polyglycol ether.

115.71 g (38.57%) of Piccolyte resin S-10 were dissolved in 79.29 g (26.43%) of Soltrol 130 and introduced into the stirring compartment of a ball mill. Then 78 g (26%) of BCM, 27 g (9%) of laurylalcohol polyglycol ether having a polymerization degree of 10 and 500 g of 1 mm quartz pearls were added and the whole was ground for 6 hours. Thereafter the BCM had a particle size of less than 5 microns. The quartz pearls were then separated by sieving.

After a storage life of 3 months the dispersion was viscous, the sediment could not be redispersed in the container and dispersed in water only with great difficulty.

EXAMPLE 2

A BCM dispersion according to the invention and containing
25% by weight of BCM
1% by weight of Ca-dodecylbenzene sulfonate (in the form of a 70% solution in i-butanol)
2% by weight of triisobutylphenol polyglycol ether ("Sapogenat T-100 ®")
6% by weight of octylphenol polyglycol ether ("Triton X-207 ®)
66% by weight of paraffinic mineral oil ("Essobayol 90 ®") was prepared in the same manner. Essobayol 90 has the following characteristics: viscosity 27.5 cp at 20° C flash point 170° C boiling range 300°–400° C paraffine content 95%

EXAMPLE 3

Another BCM dispersion had the following composition:
20.00% by weight of BCM
2.25% by weight of Ca-dodecylbenzene sulfonate (in the form of a 70% solution in isobutanol)
3.80% by weight of triisobutylphenol polyglycol ether ("Sapogenat T-100 ®")
8.75% by weight of octylphenol polyglycol ether ("Triton X-207 ®")
65.20% by weight of paraffinic mineral oil ("Essobayol 90 ®")

Commercial wettable powder based on Benomyl was used as a further comparatif agent (comparatif agent 2)

In order to demonstrate the biological efficiency the following tests were carried out, which were also confirmed by field tests.

EXAMPLE 4:

Cucumber plants were cut off above the first two true leaves. As soon as these were completely grown, the cotelydons situated below were also removed and the lower parts of the leaves were sprayed to the drip off with aqueous preparations of the compositions of examples 2 and 3 by means of a micro-applicator. Contamination by active ingredient of the upper surface of the leaves and other parts of the plant as well as the soil was thus prevented.

The comparative preparation was a composition prepared according to British Specification No. 1,190,614 (comparative agent 1) and a commercial wettable powder based on Benomyl (comparative agent 2).

The composition of the test preparations and of the comparative agents were applied in concentrations of 1000, 500, 250, 125, 60 and 30 mg each of active ingredient per liter of spraying liquid.

After drying, the upper surface of the leaves was infected with conidia of cucumber mildew (Erysiphe cichoracearum). The plants were then placed in a green house at a relative humidity of 80 to 90% and a temperature of from 23° to 25° C. After an incubation time of 14 days the plants were examined visually as to the degree of damage by cucumber mildew. The degree of damage was expressed in percent of attacked surface of the leaves compared to infected untreated controls.

From the result indicated in table 1 it is seen that the activity of the dispersion prepared according to British Patent Specification No. 1,190,614 was considerably lower than that of the oily dispersions prepared according to examples 2 and 3 of the invention. The latter dispersion was also by far superior to the commercial formulation of Benomyl.

EXAMPLE 5:

Apple seedlings in the 8-leaf-state were defoliated, except for the 4 yougest unfilded leaves, strongly infected with conidia of apple scab (Venturia inaequalis) and placed dripping wet in a climatic chamber having a relative humidity of 100% and a temperature of 20° C.

After 2 days the plants were put in a green-house adusted to a temperature of 18° C and a relative humidity of 90 to 95%.

After 3 days the lower surfaces of the leaves were sprayed to the drip off with aqueous reparations of the oily dispersions prepared according to examples 2, 3 and 4 using the same precautions as in Example 3.

A dispersion prepared according to British Patent Specification No. 1,190,614 and a usual wettable powder formulation of Benomyl (comparative agent 2) were applied as comparative agents in an analogous manner. The applied concentrations were 1000, 500, 250, 60 and 30 mg each of active ingredient per liter of spraying liquid.

After drying the plants were replaced in the greenhouse and examined visually as to the degree of damage by apple scap after an incubation time of 21 days. The degree of damage was expressed in percent of attacked surface of the leaves calculated on infected untreated the controls.

From the test result indicated in table 2 it is seen that the activity of the formulations according to the invention was considerably higher than that of the composition prepared according to British Patent Specification No. 1,190,614.

The formulations according to the invention were also superior to the composition based on Benomyl.

TABLE 1

| Composition of the Substance | % of surface of the leaves infected by cucumber mildew mg of active ingredient per liter of spraying liquor | | | | | |
|---|---|---|---|---|---|---|
| | 1000 | 500 | 250 | 125 | 60 | 30 |
| 25 % BCM-dispersion according to example 2 | 0 | 0 | 0 | 0 | 8 | 12 |
| 20 % BCM-dispersion according to example 3 | 0 | 0 | 0 | 0 | 5 | 10 |
| Comparative agent 1 BCM-dispersion according to British Patent Specification No. 1,190,614 Example 1 | 0*) | 15*) | 30 | 65 | 85 | 100 |
| Comparative agent 2 commercial wettable powder of Benomyl | 0 | 0 | 0 | 8 | 15 | 32 |
| Non-treated infected control plant | 100 | 100 | 100 | 100 | 100 | 100 |

*)marked damages of the leaves

TABLE 2

| Composition of the Substance | % of surface of the leaves infected by apple scap mg of active ingredient per liter of spraying liquor | | | | | |
|---|---|---|---|---|---|---|
| | 1000 | 500 | 250 | 125 | 60 | 30 |
| BCM-dispersion according to example 2 | 0 | 0 | 0 | 0 | 3 | 10 |
| 20 % BCM-dispersion according to example 3 | 0 | 0 | 0 | 0 | 2 | 8 |
| Comparative agent 1 BCM-dispersion according to British Patent Specification No. 1,190,614 | 0*) | 3*) | 10 | 20 | 42 | 58 |
| Comparative agent 2 Commercial wettable powder of Benomyl | 0 | 0 | 0 | 8 | 15 | 27 |
| Non-treated infected control plant | 100 | 100 | 100 | 100 | 100 | 100 |

*)marked damages by burning of the leaves

What is claimed is:

1. A fungicidal dispersion, comprising
   a. about 5 to 30 percent by weight of the compound of the formula

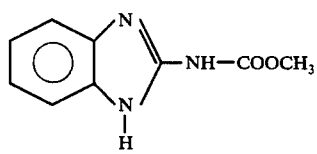

b. about 60 to 85 percent by weight of an aliphatic mineral oil having a flash point of from 65° to 180° C and a viscosity of from 1.5 to 30 centipoise at 20° C
   c. about 6 to 15 percent by weight of a combination of dispersible agents comprising from 5 to 10 percent by weight of a monoalkylphenol polyglycol ether of 8 to 12 glycol units the monoalkyl radical of which has from 8 to 12 carbon atoms and a triisobutylphenol polyglycol ether wherein the polyglycol portion has 8 to 15 glycol units and
   d. about 0.1 to 3 percent by weight of calcium monoalkylbenzene sulfonate wherein the monoalkyl radical has from 8 to 15 carbon atoms in the same.

2. A fungicidal dispersion, comprising
   a. about 5 to 30 percent by weight of the compound of the formula

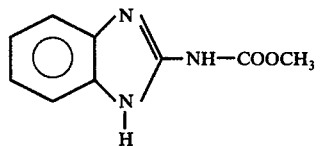

b. about 60 to 85 percent by weight of an aliphatic mineral oil having a flash point of from 65° to 180° C, a viscosity of from 1.5 to 30 centipoise at 20° C, a boiling range between 192° and 420° C and a paraffin content of about 95 percent,
   c. about 6 to 15 percent by weight of a combination of dispersible agents comprising from 5 to 10 percent by weight of an octylphenol polyglycol ether having 8 to 12 glycol units and 1 to 5 percent by weight of a triisobutylphenol polyglycol ether having an 8 to 15 degree of polymerization, and
   d. about 0.1 to 3 percent by weight of calcium dodecylbenzene sulfonate.

3. A fungicidal dispersion as claimed in claim 2 wherein the mineral oil has a viscosity of 27.5 cp at 20° C, a flash point of 170° C, a boiling range of 300°–400° C and a paraffin content of 95 percent.

* * * * *